United States Patent
Yang

(10) Patent No.: US 10,874,458 B2
(45) Date of Patent: Dec. 29, 2020

(54) MANUFACTURING METHOD FOR NON-MAGNETIC WATER-COOLED MICROWAVE ABLATION NEEDLE

(71) Applicant: NANJING VISON-CHINA MEDICAL DEVICES R & D CENTER, Jiangsu (CN)

(72) Inventor: Ting Yang, Jiangsu (CN)

(73) Assignee: NANJING VISON-CHINA MEDICAL DEVICES R & D CENTER, Jiangsu (CN)

( * ) Notice: Subject to any disclaimer, the term of this patent is extended or adjusted under 35 U.S.C. 154(b) by 603 days.

(21) Appl. No.: 15/512,464

(22) PCT Filed: Jan. 22, 2015

(86) PCT No.: PCT/CN2015/071280
§ 371 (c)(1),
(2) Date: Mar. 17, 2017

(87) PCT Pub. No.: WO2016/074344
PCT Pub. Date: May 19, 2016

(65) Prior Publication Data
US 2017/0296269 A1    Oct. 19, 2017

(30) Foreign Application Priority Data
Nov. 11, 2014    (CN) .......................... 2014 1 0631162

(51) Int. Cl.
*A61B 18/18* (2006.01)
*B21G 1/00* (2006.01)
(Continued)

(52) U.S. Cl.
CPC .......... *A61B 18/1815* (2013.01); *A61B 18/18* (2013.01); *B21G 1/003* (2013.01);
(Continued)

(58) Field of Classification Search
CPC ...... A61B 18/1815; A61B 2017/00526; A61B 2017/00577; A61B 18/18;
(Continued)

(56) References Cited

U.S. PATENT DOCUMENTS

| 5,629,380 A | * | 5/1997 | Baldwin | ................ C08G 59/68 525/113 |
| 2003/0009190 A1 | * | 1/2003 | Kletschka | ............ A61B 17/221 606/200 |

(Continued)

FOREIGN PATENT DOCUMENTS

| CN | 101631506 A | 1/2010 | |
| CN | 201775679 U | * 3/2011 | ............. A61B 18/18 |

(Continued)

OTHER PUBLICATIONS

Yang, Ting; Chinese Patent Publication, CN 201775679—"Water-cooled microwave ablation needle for bone tumor therapy", Translated on Sep. 9, 2019 (Year: 2011).*

*Primary Examiner* — Eun Hwa Kim
*Assistant Examiner* — Adam Z Minchella
(74) *Attorney, Agent, or Firm* — Maschoff Brennan

(57) ABSTRACT

The present invention relates to a method for manufacturing a nonmagnetic water-cooled microwave ablation needle. The manufacturing method is designed for a microwave ablation needle of a nonmagnetic material and has a proper process procedure, favorable assembly quality, and high production efficiency. The produced nonmagnetic water-cooled microwave ablation needle is applicable to microwave tumor ablation surgery in a nuclear magnetic resonance imaging environment, and helps a doctor in charge to clearly determine a position of a tumor, improve piercing precision, have preferable control on a whole surgery process, improve a success rate of the surgery, reduce damage on surrounding normal tissues as much as possible on the (Continued)

premise of effectively inactivating the tumor, alleviate pain of a patient, and shorten a recovery cycle.

4 Claims, 1 Drawing Sheet

(51) Int. Cl.
| | |
|---|---|
| *B23K 31/02* | (2006.01) |
| *H01P 1/04* | (2006.01) |
| *H01P 3/06* | (2006.01) |
| *H01P 11/00* | (2006.01) |
| *H01R 4/02* | (2006.01) |
| *H01R 24/40* | (2011.01) |
| *B23K 101/38* | (2006.01) |
| *B23K 103/12* | (2006.01) |
| *A61B 18/00* | (2006.01) |
| *A61B 17/00* | (2006.01) |
| *H01R 103/00* | (2006.01) |

(52) U.S. Cl.
CPC ............ *B23K 31/02* (2013.01); *H01P 1/045* (2013.01); *H01P 3/06* (2013.01); *H01P 11/005* (2013.01); *H01R 4/023* (2013.01); *H01R 4/029* (2013.01); *H01R 24/40* (2013.01); *A61B 2017/00526* (2013.01); *A61B 2018/00023* (2013.01); *A61B 2018/00577* (2013.01); *A61B 2018/1869* (2013.01); *B23K 2101/38* (2018.08); *B23K 2103/12* (2018.08); *H01R 2103/00* (2013.01)

(58) Field of Classification Search
CPC ........... A61B 2018/00023; A61B 2018/00577; A61B 2018/1869; H01P 1/045; H01P 3/06; H01P 11/005; H01P 11/001; B21G 1/003; B23K 31/02; B23K 2103/12; B23K 2101/38; H01R 4/023; H01R 4/029; H01R 24/40; H01R 2103/00
See application file for complete search history.

(56) References Cited

U.S. PATENT DOCUMENTS

| | | | |
|---|---|---|---|
| 2007/0203551 A1* | 8/2007 | Cronin | A61B 18/18 607/101 |
| 2008/0275439 A1* | 11/2008 | Francischelli | A61B 18/1402 606/34 |
| 2009/0104448 A1* | 4/2009 | Thompson | B32B 37/12 428/413 |
| 2011/0118720 A1* | 5/2011 | Turner | A61B 18/1815 606/33 |
| 2013/0317495 A1 | 11/2013 | Brannan | |
| 2015/0200254 A1* | 7/2015 | Diduck | H01L 23/3732 428/141 |

FOREIGN PATENT DOCUMENTS

| | | |
|---|---|---|
| CN | 201775679 U | 3/2011 |
| CN | 201775680 U | 3/2011 |
| CN | 203619673 U | 6/2014 |
| WO | 2006002943 A1 | 1/2006 |

\* cited by examiner

MANUFACTURING METHOD FOR NON-MAGNETIC WATER-COOLED MICROWAVE ABLATION NEEDLE

TECHNICAL FIELD

The present invention relates to a method for manufacturing a nonmagnetic water-cooled microwave ablation needle, where the manufactured ablation needle is particularly applicable to carrying out interventional treatment in a nuclear magnetic resonance environment.

RELATED ART

With the development of modern technology and oncology, in recent decades, breakthroughs have been made in microwave tumor ablation technology in China. The microwave tumor ablation utilizes that microwaves can act on a tissue, that is, can generate a thermal effect, and within a time of several to tens of minutes, a temperature at the center of a thermal field of the microwaves may reach 100° C. or above, and a tumor tissue is solidified and inactivated at a transient high temperature, thereby achieving an objective of tumor ablation treatment. The microwave tumor ablation is intervening a lesion of a human body tissue with a microwave ablation needle by enabling a front end thereof to continuously transmit microwave energy, so as to perform an operation, and because of its high efficiency, small wound, and controllable acting depth and scope size on a tissue, is applicable to ablation surgery on solid tumors of the whole body.

The microwave ablation surgery belongs to image-guided minimally invasive surgery, and currently, is generally carried out in an ultrasonic imaging environment. As a mainstream ultrasonic imaging technology, the microwave ablation surgery has limitations in terms of tumor boundary determination. In order to completely inactivate a tumor tissue, a surgery doctor in charge usually enlarges a heating scope, which usually causes a disadvantageous effect on a normal tissue of a human body, and causes a severer hidden danger if a pierced position is incorrect.

Comparatively, the nuclear magnetic resonance imaging technology has higher accuracy, and intuitiveness and clarity of its imaging are incomparable to the ultrasonic imaging technology. However, because of being limited by the existing ablation needle in terms of material technology, the nuclear magnetic resonance imaging technology cannot be used in a nuclear magnetic resonance environment, which, to some extent, limits development of the microwave ablation surgery.

SUMMARY

A technical problem the present invention attempts to resolve is to overcome the foregoing disadvantages to provide a method for manufacturing a nonmagnetic water-cooled microwave ablation needle and an ablation needle obtained according to the method.

To resolve the foregoing technical problem, a method for manufacturing a nonmagnetic water-cooled microwave ablation needle provided by the present invention includes the following steps:

S1: removing an outer conductor from head and tail ends of a coaxial cable to expose a dielectric layer, and then removing a front segment of the exposed dielectric layer to expose an inner conductor, where the outer conductor and inner conductor of the coaxial cable are both made of copper;

S2: deforming and firmly connecting a copper pole shank and the inner conductor of the coaxial cable in a cold-pressing manner, where after being connected, the pole shank and the coaxial cable have the same center;

S3: coating an outer surface of the pole shank and an inner hole of a zirconia penetrator with a ceramic adhesive, inserting the pole shank into the inner hole of the zirconia penetrator, and performing dry bonding;

S4: sheathing a copper water plugging shaft and a water delivery pipe on the coaxial cable in sequence, where a head of the water plugging shaft abuts against a rear end face of the zirconia penetrator, and a tail of the water plugging shaft is welded to the outer conductor of the coaxial cable in a sealing manner, sheathing a front end of the water delivery pipe on an outer circle of a lifting shoulder of the water plugging shaft, and fixing the front end of the water delivery pipe to the water plugging shaft in a welding manner, where there should be no dry joint;

S5: sheathing a front end of a copper needle bar on an outer circle of the zirconia penetrator, fixing the needle bar to the zirconia penetrator and the water plugging shaft by using an epoxy resin adhesive, and performing rivet connection;

S6: welding a copper radio frequency coaxial connector to a tail of the coaxial cable; and S7: mounting a water inlet sleeve, a water inlet chamber, a water outlet chamber, a water nozzle, and a handle.

To resolve the foregoing technical problem, the present invention further includes the following features:

1. In step S3, a dry bonding method includes performing natural drying in the air for 2 to 4 hours, and then, performing heating in a thermostatic drying chamber for 2 to 4 hours, where a temperature in the thermostatic drying chamber is 93° C.

2. In step S5, a surface of the water plugging shaft and an outer circle of a rear shaft of the zirconia penetrator are respectively coated with the epoxy resin adhesive, the needle bar is pushed to a tail face of the penetrator, there should be no gap, the ablation needle is placed into a thermostatic drying chamber to be heated for 25 to 35 minutes, and a temperature inside the thermostatic drying chamber ranges from 140 to 160° C.

3. A front of the water delivery pipe is an inclined plane, a back is provided with a water outlet hole, the water plugging shaft is of a two-segment type, inner hole diameters of two segments are the same and adapt to the outer conductor of the coaxial cable, an outer diameter of a front segment adapts to an inner diameter of the needle bar, an outer diameter of a rear segment is smaller the inner diameter of the needle bar to form the outer circle of the lifting shoulder, and a front end of the inclined plane of the water delivery pipe is fixed to the outer circle of the lifting shoulder of the water plugging shaft in a welding manner.

4. An outer diameter of an outer circle of a tail of the zirconia penetrator is equal to an outer diameter of the front segment of the water plugging shaft.

In addition, the present invention further protects an ablation needle or a main component of an ablation needle manufactured by using the foregoing manufacturing method.

The ablation needle mainly includes a zirconia penetrator, a pole shank, a coaxial cable, a water plugging shaft, a water delivery pipe, and a needle bar, where the pole shank is inserted into a central hole of the penetrator, a rear end of the pole shank is fixedly connected to an inner conductor of the coaxial cable in a cold-pressing manner, the water plugging shaft is sheathed on the coaxial cable, a head thereof abuts against a rear end face of the zirconia penetrator, a tail is welded to an outer conductor of the coaxial cable in a sealing manner, a front end of the water delivery pipe is sheathed on an outer circle of the water plugging shaft and is fixed to the water plugging shaft in a welding manner, a front end of the needle bar is sheathed on an outer circle of the zirconia penetrator, and the needle bar is fixed to the zirconia penetrator and the water plugging shaft in a bonding manner by using an epoxy resin adhesive; and a radio frequency coaxial connector is welded to a tail of the coaxial cable.

The microwave ablation needle of the present invention is manufactured by using a nonmagnetic material, is applicable to microwave tumor ablation surgery in a nuclear magnetic resonance imaging environment, and helps a doctor in charge to clearly determine a position of a tumor, improve piercing precision, have preferable control on a whole surgery process, improve a success rate of the surgery, reduce damage on surrounding normal tissues as much as possible on the premise of effectively inactivating the tumor, alleviate pain of a patient, and shorten a recovery cycle.

With regard to such a microwave ablation needle of a nonmagnetic material, the present invention proposes a corresponding manufacturing solution, which has a proper process procedure, favorable assembly quality, and a high success rate. The ablation needle of the present invention has a simple structure, parts are optimized and reduced to some extent, and assembly efficiency and quality are improved. The experiments show that quality of an assembled product meets design requirements.

BRIEF DESCRIPTION OF THE DRAWINGS

The present invention is further described below by referring to the accompanying drawings.

REFERENCE SIGNS

1—zirconia penetrator, 2—pole shank, 3—coaxial cable, 4—water plugging shaft, 5—water delivery pipe, 6—needle bar, 7—inner conductor, 8—outer conductor, 9—dielectric layer, 10—water outlet chamber, 11—water inlet chamber, 12—water nozzle, 13—water resisting ring, 14—fixing sleeve.

DETAILED DESCRIPTION OF THE PREFERRED EMBODIMENTS

Figure 1:
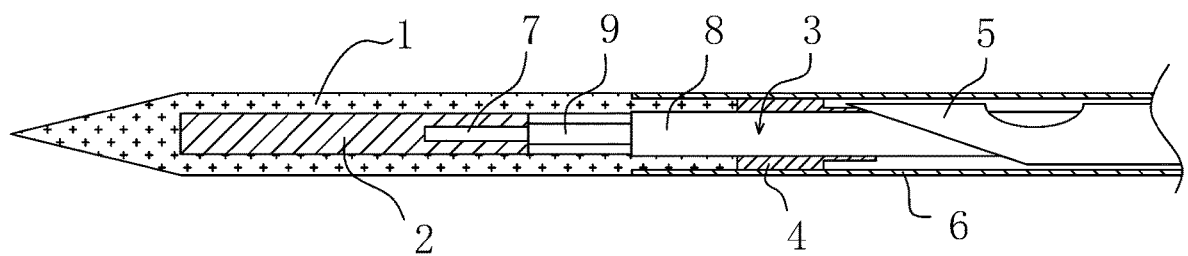
FIG. 1 is a sectional view of a front end of a nonmagnetic water-cooled ablation needle of the present invention.
Figure 2:
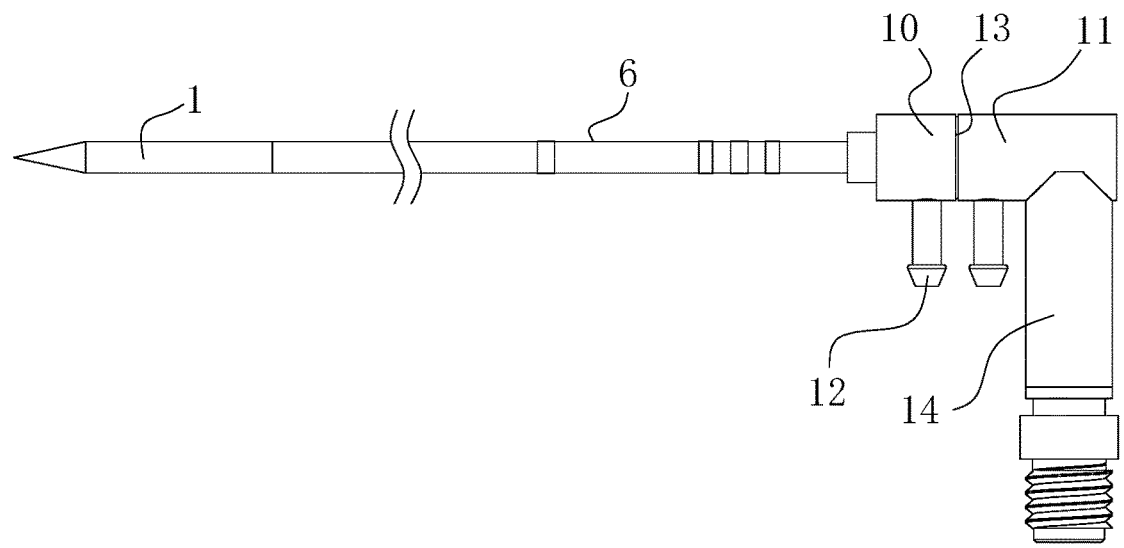
FIG. 2 is an overall schematic structural diagram of a nonmagnetic water-cooled ablation needle of the present invention.

As shown in FIG. 1 and FIG. 2, a nonmagnetic water-cooled microwave ablation needle to be manufactured in an embodiment of the present invention mainly includes a zirconia penetrator 1, a pole shank 2, a coaxial cable 3, a water plugging shaft 4, a water delivery pipe 5, and a needle bar 6, where the pole shank 2 is inserted into a central hole of the penetrator, a rear end of the pole shank 2 is fixedly connected to an inner conductor 7 of the coaxial cable 3 in a cold-pressing manner, the water plugging shaft 4 is sheathed on the coaxial cable 3, a head thereof abuts against a rear end face of the zirconia penetrator 1, a tail is welded to an outer conductor 8 of the coaxial cable 3 in a sealing manner, a front end of the water delivery pipe 5 is sheathed on an outer circle of the water plugging shaft 4 and is fixed to the water plugging shaft 4 in a welding manner, a front end of the needle bar 6 is sheathed on an outer circle of the zirconia penetrator 1, and the needle bar 6 is fixed to the zirconia penetrator 1 and the water plugging shaft 4 in a bonding manner by using an epoxy resin adhesive; and a radio frequency coaxial connector is welded to a tail of the coaxial cable 3. As shown in the drawing, a front of the water delivery pipe is an inclined plane, a back is provided with a water outlet hole, the water plugging shaft 4 is of a two-segment type, inner hole diameters of two segments are the same and adapt to the outer conductor 8 of the coaxial cable 3, an outer diameter of a front segment adapts to an inner diameter of the needle bar 6, an outer diameter of a rear segment is smaller the inner diameter of the needle bar 6 to form an outer circle of a lifting shoulder, and a front end of the inclined plane of the water delivery pipe is fixed to the outer circle of the lifting shoulder of the water plugging shaft 4 in a welding manner. An outer diameter of an outer circle of a tail of the zirconia penetrator 1 is equal to an outer diameter of the front segment of the water plugging shaft 4. In the drawing, 13 is a water resisting ring, and 14 is a fixing sleeve.

A method for manufacturing a nonmagnetic water-cooled microwave ablation needle according to this embodiment includes the following steps:

S1: Remove an outer conductor 8 from head and tail ends of a coaxial cable 3 to expose a dielectric layer 9, and then remove a front segment of the exposed dielectric layer 9 to expose an inner conductor 7, where the outer conductor 8 and inner conductor 7 of the coaxial cable 3 are both made of copper.

S2: Deform and firmly connect a copper pole shank 2 and the inner conductor 7 of the coaxial cable 3 in a cold-pressing manner, where after being connected, the pole shank 2 and the coaxial cable 3 have the same center.

S3: Coat an outer surface of the pole shank 2 and an inner hole of a zirconia penetrator 1 with a ceramic adhesive, insert the pole shank 2 into the inner hole of the zirconia penetrator 2, and perform dry bonding.

In this step, a dry bonding method includes performing natural drying in the air for 2 to 4 hours, and then, performing heating in a thermostatic drying chamber for 2 to 4 hours, where a temperature in the thermostatic drying chamber is 93° C.

S4: Sheath a copper water plugging shaft 4 and a water delivery pipe 5 on the coaxial cable 3 in sequence, where a head of the water plugging shaft 4 abuts against a rear end face of the zirconia penetrator 1, and a tail of the water plugging shaft 4 is welded to the outer conductor 8 of the coaxial cable 3 in a sealing manner, sheath a front end of the water delivery pipe 5 on an outer circle of a lifting shoulder of the water plugging shaft 4, and fix the front end of the water delivery pipe 5 to the water plugging shaft 4 in a welding manner, where there should be no dry joint;

S5: Sheath a front end of a copper needle bar 6 on an outer circle of the zirconia penetrator 1, fix the needle bar 6 to the zirconia penetrator 1 and the water plugging shaft 4 by using an epoxy resin adhesive, and perform rivet connection.

In this step, a surface of the water plugging shaft 4 and an outer circle of a rear shaft of the zirconia penetrator 1 are respectively coated with the epoxy resin adhesive, the needle bar 6 is pushed to a tail face of the penetrator, there should be no gap, the ablation needle is placed into a thermostatic drying chamber to be heated for 25 to 35 minutes, and a temperature inside the thermostatic drying chamber ranges from 140 to 160° C.

S6: Weld a copper radio frequency coaxial connector to a tail of the coaxial cable 3.

S7: Mount a water inlet sleeve, a water inlet chamber 11, a water outlet chamber 10, a water nozzle 12, and a handle.

In addition to the foregoing embodiments, the present invention may also include other implementation manners. Any technical solutions formed by means of equivalent replacement or equivalent transformation all fall within the protection scope claimed by the present invention.

What is claimed is:

1. A method for manufacturing a nonmagnetic water-cooled microwave ablation needle, comprising the following steps:
    S1: removing an outer conductor from a head and tail ends of a coaxial cable to expose a dielectric layer, and then removing a front segment of the exposed dielectric layer to expose an inner conductor, wherein the outer conductor and inner conductor of the coaxial cable are both made of copper;
    S2: deforming and firmly connecting a copper pole shank and the inner conductor of the coaxial cable in a cold-pressing manner, wherein after being connected, the pole shank and the coaxial cable have the same center;
    S3: coating an outer surface of the pole shank and an inner hole of a zirconia penetrator with a ceramic adhesive, inserting the pole shank into the inner hole of the zirconia penetrator, and performing dry bonding;
    S4: sheathing a copper water plugging shaft and a water delivery pipe on the coaxial cable in sequence, wherein a head of the water plugging shaft abuts against a rear end face of the zirconia penetrator, and a tail of the water plugging shaft is welded to the outer conductor of the coaxial cable in a sealing manner, sheathing a front end of the water delivery pipe on an outer circle of a lifting shoulder of the water plugging shaft, and fixing the front end of the water delivery pipe to the water plugging shaft in a welding manner, wherein there is no dry joint;
    S5: sheathing a front end of a copper needle bar on an outer circle of the zirconia penetrator, fixing the needle bar to the zirconia penetrator and the water plugging shaft by using an epoxy resin adhesive, and performing rivet connection;
    S6: welding a copper radio frequency coaxial connector to a tail of the coaxial cable; and
    S7: mounting a water inlet sleeve, a water inlet chamber, a water outlet chamber, a water nozzle, and a handle; and
        wherein, in step S5, a surface of the water plugging shaft and an outer circle of a rear shaft of the zirconia penetrator are respectively coated with the epoxy resin adhesive, the needle bar is pushed to a tail face of the penetrator, there is no gap, the ablation needle is placed into a thermostatic drying chamber to be heated for 25 minutes to 35 minutes, and a temperature inside the thermostatic drying chamber ranges from 140° C. to 160° C.

2. The method for manufacturing the nonmagnetic water-cooled microwave ablation needle according to claim 1, wherein in step S3, a dry bonding method comprises performing natural drying in the air for 2 to 4 hours, and then, performing heating in a thermostatic drying chamber for 2 to 4 hours, wherein a temperature in the thermostatic drying chamber is 93° C.

3. The method for manufacturing the nonmagnetic water-cooled microwave ablation needle according to claim 1, wherein:
    a front of the water delivery pipe is an inclined plane,
    a back is provided with a water outlet hole,
    the water plugging shaft is of a two-segment type,
    inner hole diameters of two segments are the same and adapt to the outer conductor of the coaxial cable,
    an outer diameter of a front segment adapts to an inner diameter of the needle bar,
    an outer diameter of a rear segment is smaller than the inner diameter of the needle bar to form the outer circle of the lifting shoulder, and
    a front end of the inclined plane of the water delivery pipe is fixed to the outer circle of the lifting shoulder of the water plugging shaft in a welding manner.

4. The method for manufacturing the nonmagnetic water-cooled microwave ablation needle according to claim 1, wherein an outer diameter of an outer circle of a tail of the zirconia penetrator is equal to an outer diameter of the front segment of the water plugging shaft.

\* \* \* \* \*